US006623475B1

(12) United States Patent
Siess

(10) Patent No.: US 6,623,475 B1
(45) Date of Patent: Sep. 23, 2003

(54) BLOOD PUMP WITHOUT BEARING

(75) Inventor: Thorsten Siess, Wuerselen (DE)

(73) Assignee: Impella CardioSystems AG, Aschen (DE)

( * ) Notice: Subject to any disclaimer, the term of this patent is extended or adjusted under 35 U.S.C. 154(b) by 0 days.

(21) Appl. No.: 09/856,628

(22) PCT Filed: Nov. 17, 1999

(86) PCT No.: PCT/EP99/08835

§ 371 (c)(1),
(2), (4) Date: May 22, 2001

(87) PCT Pub. No.: WO00/32256

PCT Pub. Date: Jun. 8, 2000

(30) Foreign Application Priority Data

Dec. 2, 1998 (DE) ..................................... 298 21 565 U

(51) Int. Cl.$^7$ ................................................. A61K 9/22
(52) U.S. Cl. ..................... 604/891.1; 415/104; 417/420
(58) Field of Search ........................... 604/890.1, 891.1, 604/131; 415/104, 106, 111, 900; 417/420, 423.7, 423.12

(56) References Cited

U.S. PATENT DOCUMENTS

| 5,106,263 A | * | 4/1992 | Irie ............................. 415/106 |
| 5,290,236 A | | 3/1994 | Mathewson |
| 5,385,581 A | | 1/1995 | Bramm et al. |
| 6,030,188 A | * | 2/2000 | Nojiri et al. ................. 415/900 |
| 6,074,180 A | * | 6/2000 | Khanwilkar et al. ........ 415/900 |
| 6,227,797 B1 | * | 5/2001 | Watterson et al. ........... 415/107 |
| 6,302,661 B1 | * | 10/2001 | Khanwilkar et al. ........ 415/900 |
| 6,394,769 B1 | * | 5/2002 | Bearnson et al. ............ 415/900 |

FOREIGN PATENT DOCUMENTS

| DE | 43 21 260 C1 C1 | 3/1995 |
| DE | 196 13 388 A1 | 4/1996 |
| EP | 0 451 376 B1 B1 | 6/1996 |
| WO | WO 98/04834 A1 | 2/1998 |

* cited by examiner

Primary Examiner—Edward K. Look
Assistant Examiner—John K Fristoe, Jr.
(74) Attorney, Agent, or Firm—Fulwider Patton Lee & Utecht, L.L.P.

(57) ABSTRACT

The blood pump comprises a pump casing (10) in which an impeller (16) is installed without any bearing. Said impeller (16) is rotated via a magnetic coupling (32,36) by an external magnetic driving means (33). The impeller is radially centered via the magnetic coupling (32,36). The lower side (30) of the blades (19) of the impeller is configured as supporting surface (30) sloping towards the trailing end. In this way a hydrodynamical supporting effect is attained during rotation such that the impeller (16) raises from the bottom surface (12) of the pump casing (10). Since no bearings and sealings are provided on the pump casing the danger of thrombosis and the danger of penetration of foreign bodies in the form of abrasive particles into the blood is reduced.

12 Claims, 6 Drawing Sheets

BLOOD PUMP WITHOUT BEARING

BACKGROUND OF THE INVENTION

The invention relates to a blood pump without bearing, operating according to the rotary pump principle, for temporary or long-term blood conveyance.

For temporary short-term blood conveyance extracorporeal blood pumps are used which comprise a rotationally driven impeller. Said impeller is supported on bearings in the pump casing. Examples of such blood pumps are described in EP 0 451 376 B1 and DE 43 21 260 C1. The impeller is driven via a magnetic coupling by a rotating rotor located outside the pump casing. The bearings supporting the impeller pose a problem in connection with the blood pump since thrombosis may occur at the bearings. Further, there is the danger of abrasive particles of the bearings contaminating the blood. Seals designed to protect the bearings against penetration of blood have also turned out to be unsuitable for the medium-term to long-term use (days to years). Blood pumps with mechanical support of the impeller are not suited for the long-term use for the aforementioned reasons. Pump systems having magnetic bearings (U.S. Pat. No. 5,385,581 A, DE 196 13 388 A1) which contactlessly support the impeller in an electromagnetic bearing means require a considerable controlling effort and a voluminous configuration because of the complex supporting structure where additional energy must be supplied to a large extent due to the active impeller centering.

BRIEF SUMMARY OF THE INVENTION

It is an object of the invention to provide a blood pump having a rotor rotating in a pump casing where the danger of blood contamination and thrombosis minimized.

This object is solved according to the invention with the features stated in claim 1.

The blood pump according to the invention is a blood pump without bearing which is not provided with any mechanical bearings. The impeller is freely movable within a limited clearance in the pump casing. The impeller is rotated by an external magnetic driving means thus being self-centering. At least a front side of the blades comprises supporting surfaces which hydrodynamically lift the impeller during rotation. The static force of attraction of the permanent magnets in the impeller and the driving means tends to press the impeller against the pump casing wall facing the driving means. However, the supporting surfaces in the impeller cause the impeller to be lifted from the bottom surface during rotation such that the impeller slides on a blood cushion thus being kept at a distance from the wall. The impeller without bearing is passively centered in the pump casing via permanent magnets in combination with hydrodynamically acting driving forces. The lateral centering of the impeller is also effected by the magnets cooperating with the driving means. In this way it is possible to create a blood pump without bearing and shaft where the impeller is suspended in the pump casing.

The blood pump without bearing according to the invention offers the advantage that due to the fact that no bearings and sliding seals are provided the risk of thrombosis of the blood and penetration of foreign bodies into the blood is reduced. Thus the blood pump according to the invention cannot only be used as an extracorporeal blood pump for short-term application but also as an implantable blood pump for long-term operation. The blood pump is operable with high efficiency due to the low centering-induced losses wherein the required capacity lies in the range of 6 W under physiologically relevant operating conditions such that the pump has a long service life even when configured as a battery-operated portable device.

The impeller may comprise a straight continuous passage extending from the inlet to a bottom wall of the pump casing. Thus the impeller is provided with vanes on both sides.

Preferably, the impeller blades are arranged such that they protrude to opposite sides from the circumferential wall of a disk-shaped or cone-shaped supporting body. The impeller does not form a disk which would, together with the bottom wall of the pump casing, define a narrow gap. This also reduces the risk of thrombosis. In all areas of the pump casing a blood flow is maintained without there being the danger of dead water areas.

As seen from the top the blades are of essentially triangular configuration and comprise the blade-side magnets. The triangular form of the blades allows the blade volume to increase with increasing radius such that the fluid passage area available between the blades can be kept constant on all radii. Thus the conicality of the pump casing, which would be required to ensure that on all circumferential circles approximately the same volume is available, is reduced or eliminated.

The blood pump according to the invention is a centrifugal pump where the outlet is arranged essentially tangentially to the outer edge of the pump casing. Since the maximum pressure prevails in the outlet a radial force is produced which tends to press the impeller away from the outlet. To counteract this decentering force a peripheral ring diffusor is provided on the pump casing according to a preferred aspect of the invention, the ring diffusor ending in a tangential outlet. Said ring diffusor is a helical duct which causes the pressure prevailing in the outlet to be distributed over the circumference of the pump casing thus having a centering effect on the impeller.

BRIEF DESCRIPTION OF THE DRAWINGS

Hereunder embodiments of the invention are explained in detail with reference to the drawings in which.

DETAILED DESCRIPTION OF THE INVENTION

Figure 1:
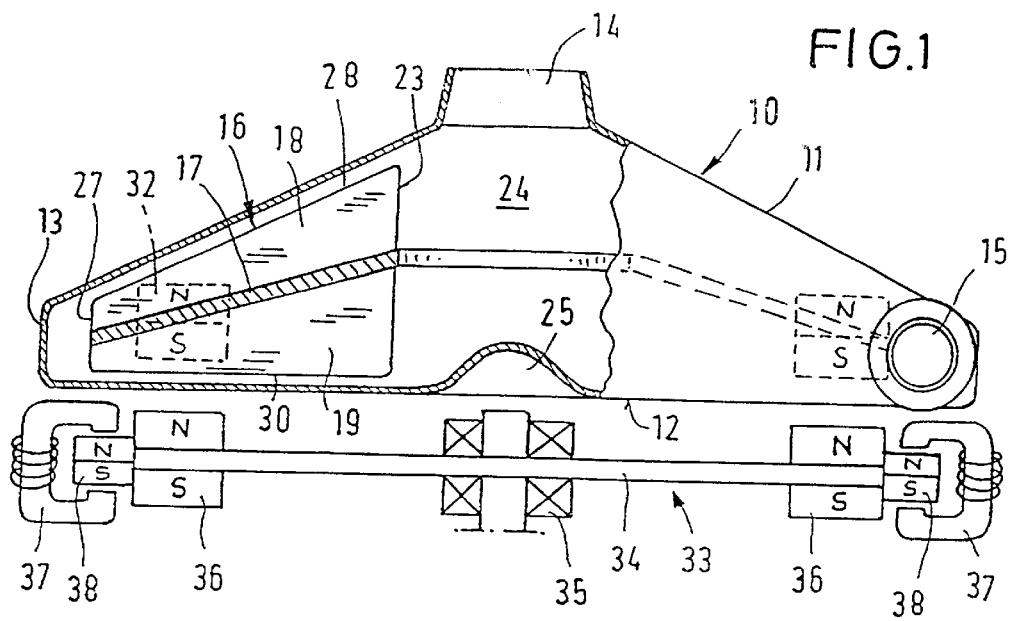
FIG. 1 shows a schematic longitudinal section across a first embodiment of the blood pump.
Figure 2:
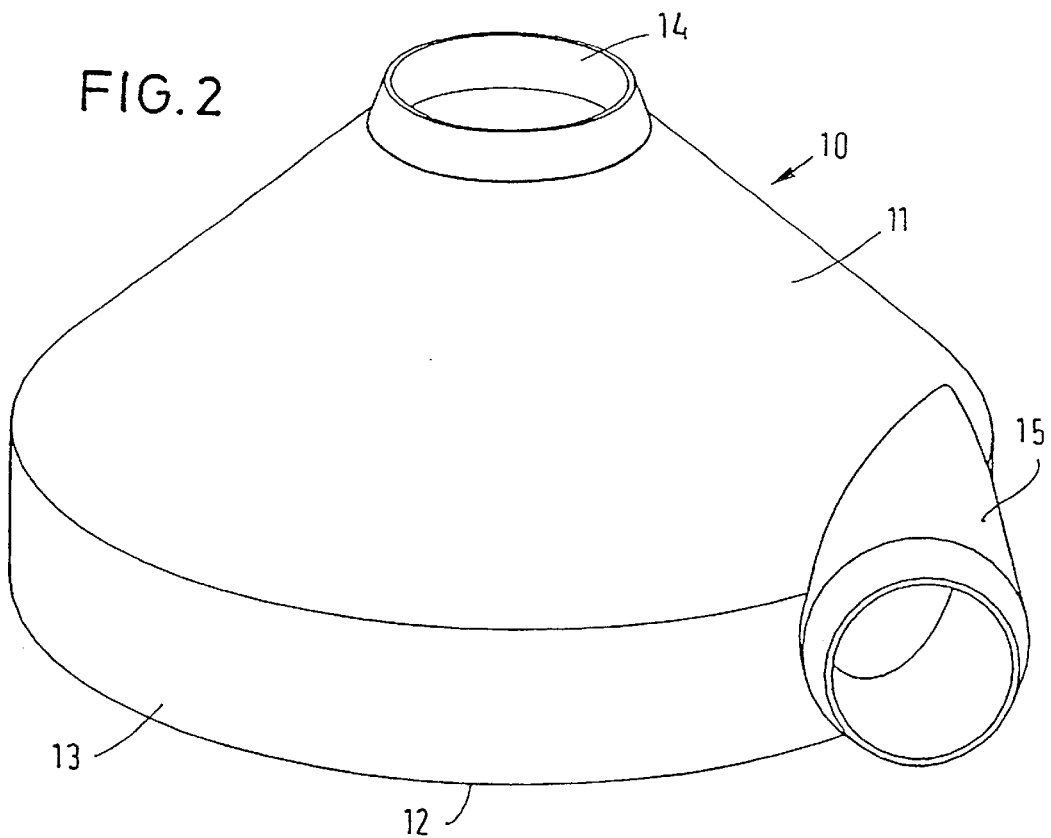
FIG. 2 shows a perspective view of the pump casing of the blood pump shown in FIG. 1.
Figure 3:
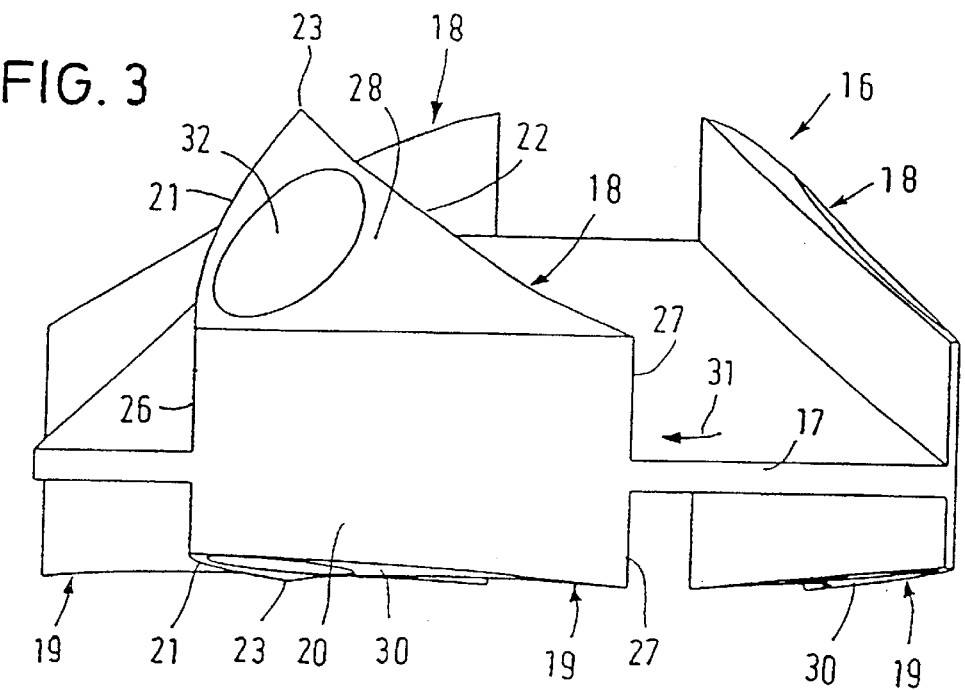
FIG. 3 shows a view of the impeller of the pump shown in FIG. 1.
Figure 4:
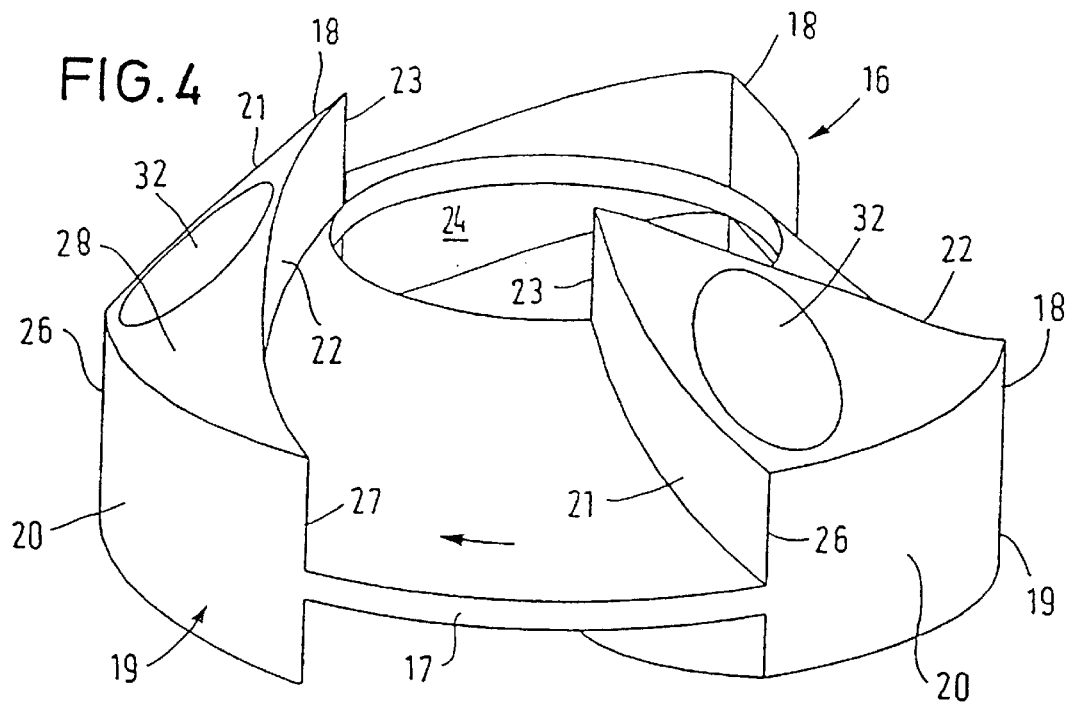
FIG. 4 shows another perspective view of the impeller of the pump shown in FIG. 1.

The blood pump shown in FIG. 1 comprises a pump casing 10 having a truncated circumferential wall 11, an essentially flat bottom wall 12 and a peripheral cylindrical wall 13 extending between said bottom wall 12 and said circumferential wall 11. The blood is supplied via the axial inlet 14 to the pump casing and leaves the latter via the tangential outlet 15 on the outer casing circumference.

In the pump casing 10 an impeller 16 is rotatably arranged. Said impeller comprises a truncated supporting body 17 whose slope is approximately half as large as that of the circumferential wall 11. The supporting body 17 is made of surface material of approximately identical thickness at all locations. On the supporting body 17 blades 18,19 protruding to the top and to the bottom are arranged wherein the upper blades 18 and the lower blades 19 are congruent as seen from the top, i.e. they have the same projection surfaces.

Said blades 18,19 are of triangular configuration as seen from the top and comprise a convex circumferential surface 20 coinciding with the circumferential circle of the supporting body 17, a convex leading surface 21 leading in the direction of rotation, and a concave inner surface 22. Said convex leading surface 21 coincides with the concave inner surface 22 at the inner edge 23. The circle on, which lie the inner edges 23 of the three blade pairs, form the limit of a circular passage 24 arranged in axial extension of the inlet 14. This means that the impeller 16 is open in its center such that a direct axial passage 24 extends down to the bottom wall 12 wherein a central raised portion 25 extending into said passage 24 is provided in the bottom wall 12. The cross-section of the passage 24 is at least as large as that of the inlet 14.

When the impeller rotates, the respective inner edge 23 precedes the outer edge 26 of the same leading surface 21. This means that the leading surface 21 presses the medium radially to the outside by setting said medium into a swirling motion. The trailing edge 27 moves along the same path as the leading edge 26.

The upper side 28 of the upper blades 18 moves in a truncated plane having the same cone angle as the circumferential surface 11 of the pump casing. Between the upper sides 28 of the blades and the conical circumferential surface 11 of the pump casing a gap is formed which provides the play required for axial movement of the impeller.

The lower sides of the lower blades 19 form supporting surfaces 30 which lift the impeller from the bottom wall 12 of the pump casing when the impeller rotates in the direction indicated by arrow 31. Said supporting faces are formed in that on the lower side of the blade the lower edge of the leding surface 21 is positioned at a larger distance to the bottom wall 12 than at the trailing end, namely at the edge 27. In this way a gap is formed between the supporting surface 30 and the bottom wall 12, the gap decreasing towards the trailing end such that fluid in the gap tends to lift the impeller. Further, the vertical height of the gap above the bottom wall increases from the inner edge 23 towards the outside whereby the impeller is also radially centered. The inclination angle α of the supporting surface 30 in the circumferential direction is approximately 2 to 40°.

The blades 18,19 which are of triangular configuration as seen from the top are each provided with a magnet 32 with north pole N and south pole S. Said magnet extends through the two blades 18,19.

The blood pump is driven by an external magnetic driving means 33 onto which the pump casing 10 is placed. Said driving means comprises a rotor 34 supported in bearings 35 and being provided with magnets 36 on its circumference. Each of said magnets 36 attracts a magnet 32 located in the pump casing 10. The rotor 34 is rotated by stationary electromagnets 37. Each electromagnet 37 comprises a U-shaped yoke through which passes a magnet 38 arranged on the circumference of the rotor 34. The poles of the electromagnets 37 are cyclically changed such that they generate a rotating magnetic field carrying along the rotor 34. Via the magnetically coupled magnets 32 and 36 the rotor 34 rotates the impeller 16. All parts of the impeller 16, with the exception of the magnets 32, are made of plastic material or another nonmagnetic material.

The type of magnet arrangement of the rotor magnet 32 at the drive magnet 36 results in a radial centering of the impeller 16. Thus 2 cartesian axes and 3 rotating axes are defined. The last remaining degree of freedom in the direction of magnetic attraction is fixed by the convergent gap formed between the supporting wall 30 and the bottom wall 12 and extending in circumferential direction. Thus the impeller, when rotating, raises from the bottom wall 12 against the magnetic attraction. When a sufficient circumferential velocity of the impeller has been reached, a blood film capable of bearing forms in the convergent gap and the impeller is suspended in the pump casing without mixed friction.

Figure 5:
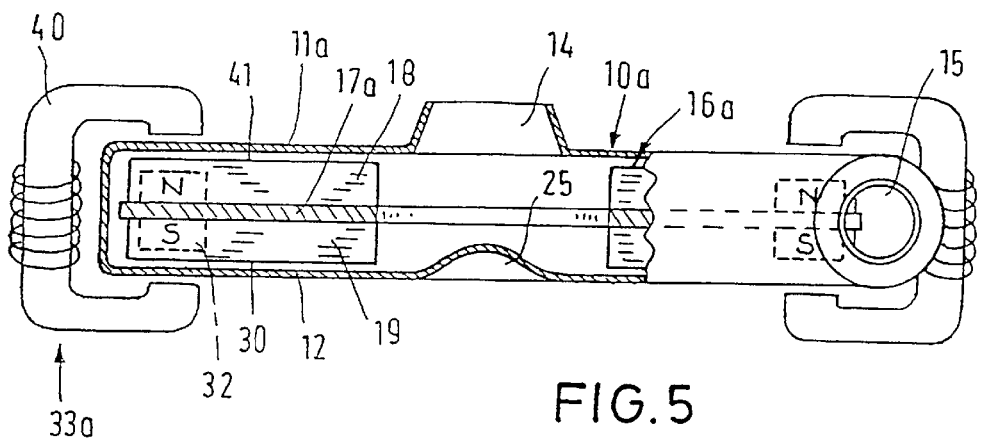
FIG. 5 shows a second embodiment of the blood pump.

In the embodiment shown in FIG. 5 the casing 10a comprises a flat bottom wall 11 and a flat upper wall 11a extending essentially in parallel to the former. The supporting body 17a, from which the blades 18,19 protrude to the top and to the bottom, is a flat disk.

According to FIG. 5 the external driving means 33a comprises electromagnets 40 distributed on the circumference of the pump casing 10a and generating a peripheral magnetic field. The yokes of the electromagnets 40 directly act upon the magnets 32 of the impeller 16a. Here, too, the magnets do not only carry out the rotary drive of the impeller but also its radial centering. For axial centering of the impeller the blades are provided with an inclined supporting surface 30 on their lower side and with an inclined supporting surface 41 on their upper side, said supporting surfaces forming, together with the upper wall 11a of the pump casing, a convergent centering gap.

Figure 6:
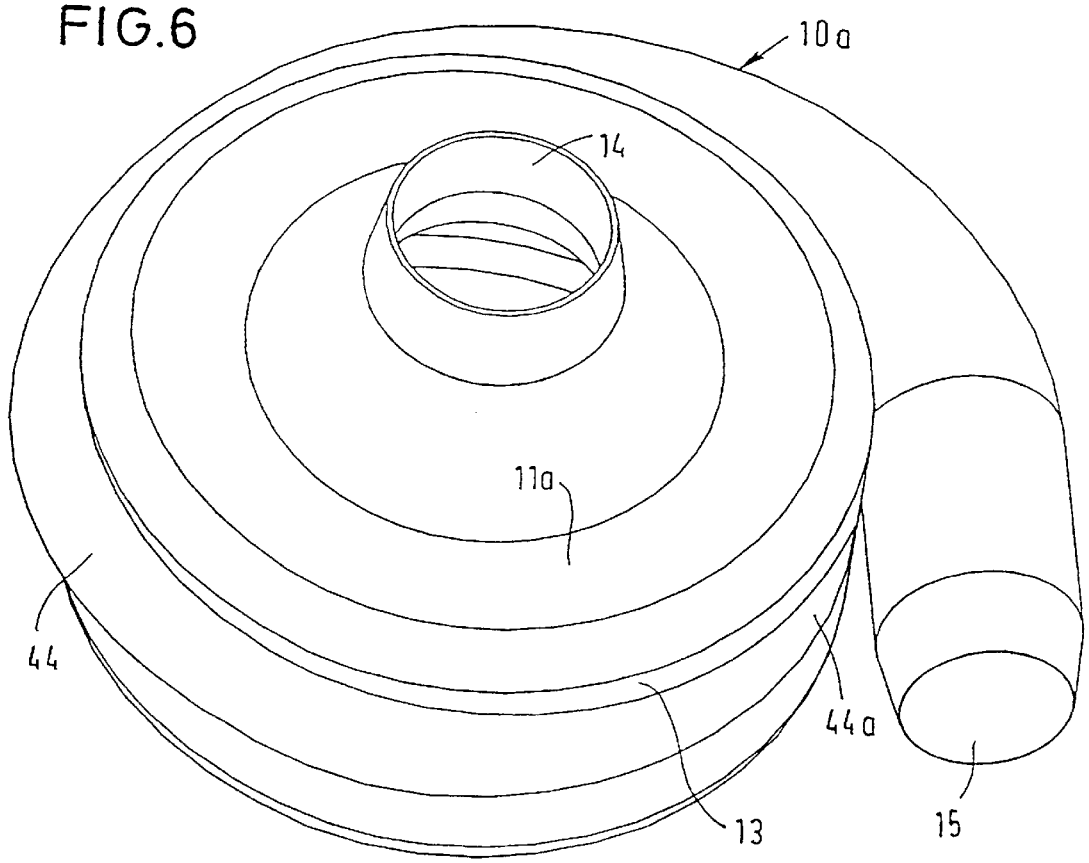
FIG. 6 shows a perspective view of the pump casing of the pump shown in FIG. 5.
Figure 7:
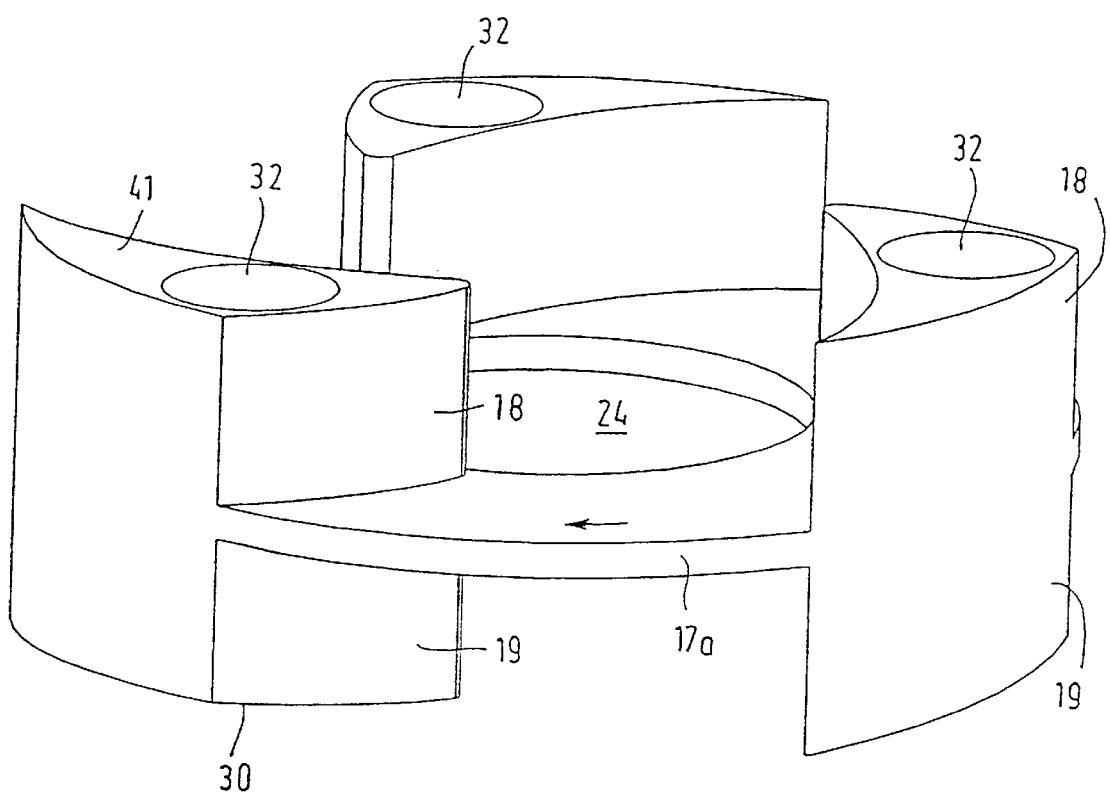
FIG. 7 shows a perspective view of the impeller of the pump shown in FIG. 5.

The blades 18,19 have the blade form shown in FIG. 7 deviating from that of the first embodiment in that the vanes are curved in forward direction as seen in the direction of rotation. In all cases the blades extend up to the passage 24 and the blade width (in circumferential direction) increases from the passage 24 towards the outside such that each blade has its maximum width at the edge of the supporting body 17 and 17a, respectively. According to FIG. 6 the pump casing 10a generally has the form of a flat cylinder with a flat upper wall 11a and a cylindrical circumferential wall 13. Since during rotation of the impeller 16a the maximum pressure builds up in the outlet 15 it may happen that this pressure presses the impeller against the pump casing side located opposite to the outlet. To compensate for this pressure force a ring diffusor 44 extends around the circumference of the pump casing, said ring diffusor 44 completely enclosing the circumference of the pump casing and being configured as a helical bulge whose cross-section continuously enlarges from the inlet end 44a towards the outlet 15.

Figure 8:
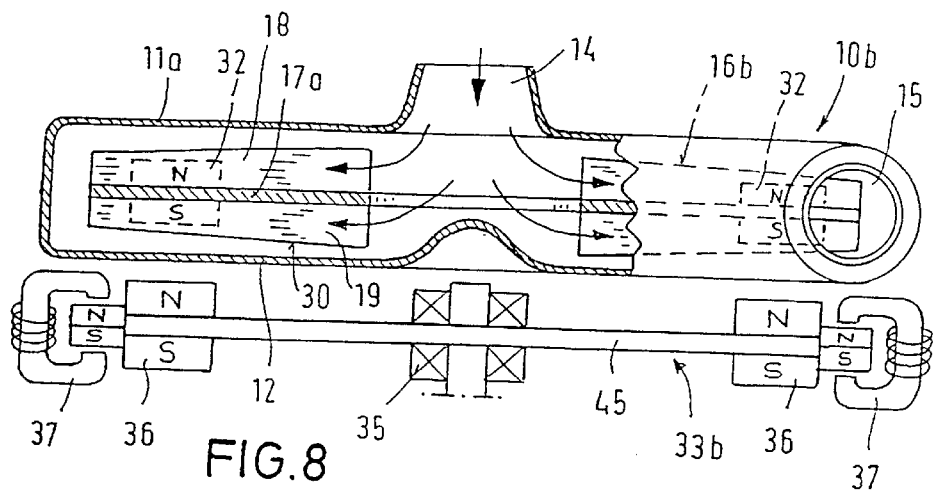
FIG. 8 shows a third embodiment of the blood pump.
Figure 9:
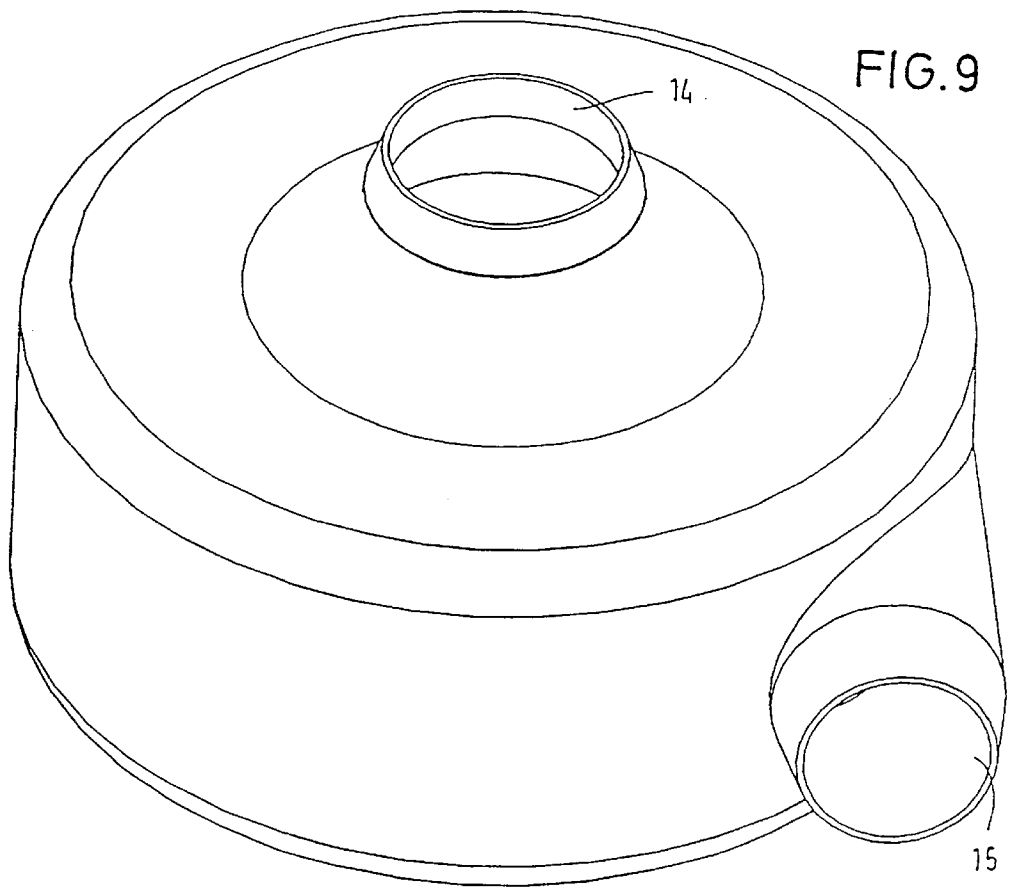
FIG. 9 shows the pump casing of the blood pump shown in FIG. 8.
Figure 10:
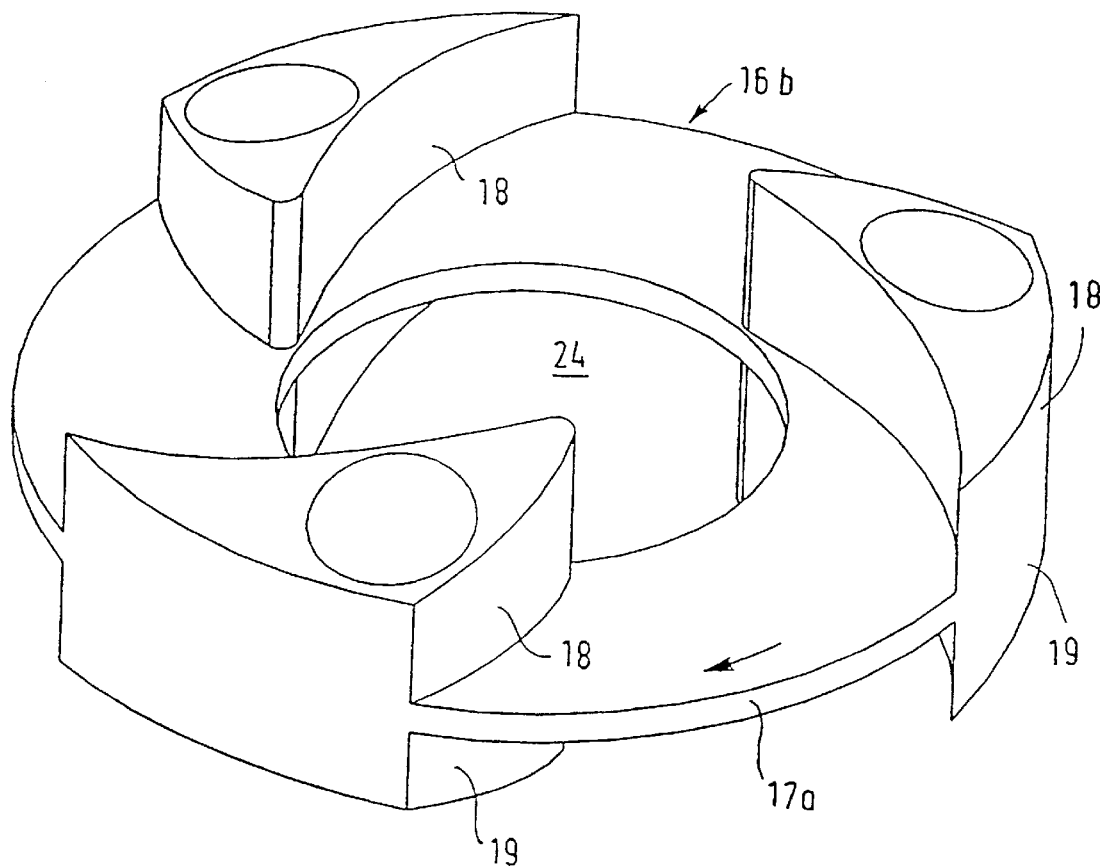
FIG. 10 shows the impeller of the blood pump shown in FIG. 8.

The embodiment shown in FIGS. 8 to 10 corresponds to a large extent to that shown in FIGS. 5 to 7. The pump casing 10b is essentially configured as a flat cylinder with a flat upper side 11a and a flat bottom wall 12. The lower side of the lower blades 19 forms a hydrodynamical supporting surface 30 which increases, as in the previous embodiments, towards the leading edge. Further, the supporting surface 30 shown in FIG. 8 increases towards the outside.

The driving means 33b comprises a disk rotor motor 45 supported in bearings 35 and being provided with magnets 36 which cooperate with the magnets 32 of the impeller 16b.

What is claimed is:

1. A blood pump without bearing, having a pump casing comprising an axial inlet and an outlet disposed on its circumference, and having an impeller rotatably arranged in said pump casing, said impeller being provided with magnets adapted to cooperate with an external magnetic driving means, wherein the impeller is freely movable within a limited clearance in the pump casing, and the blades on the lower side of the impeller facing the driving means comprise hydrodynamically lifting support surfaces, characterized in that, as seen from the top, the blades are of essentially triangular configuration, wherein the blade width increases with increasing radius and wherein the blades have a convex outer surface on the circular border of a supporting body.

2. A blood pump comprising:

a housing including an axial inlet and tangential outlet on its circumference, and upper and lower surfaces substantially parallel to one another;

an impeller floating freely within said housing without bearing when rotating therein about an axis of rotation, the impeller comprising a disc-shaped support body and a plurality of blades supported on the support body, the blades having a magnet disposed therein and hydrodynamic lifting surfaces on a lower surface thereof; and a magnetic drive external to the housing, said magnetic drive system cooperating with the magnets disposed on the blades of the impeller to bias the impeller to rotate about its axis of rotation.

3. The blood pump of claim 2 wherein the blades on the impeller have a triangular configuration when viewed from above and including a leading surface, a trailing surface, a leading edge at an outer radius, a trailing edge at an outer radius, and a coincident leading edge and trailing edge at an inner radius, where the leading edge at the outer radius precedes the leading edge at the inner radius in the direction of rotation of the impeller.

4. The blood pump of claim 2 wherein the disk-shaped support body extends substantially to a cylindrical wall of the housing.

5. A blood pump comprising:

a housing including an axial inlet and tangential outlet on its circumference;

an impeller floating freely within said housing without bearing when rotating therein about an axis of rotation, the impeller comprising a support body and a plurality of blades supported on the support body, the blades having a magnet disposed therein and hydrodynamic lifting surfaces on a lower surface thereof, the blades further comprising a triangular configuration when viewed from above and including a leading surface, a trailing surface, a leading edge at an outer radius of the leading surface, a trailing edge at an outer radius of the trailing surface, and a coincident leading edge and trailing edge at an inner radius where the leading surface and trailing surface converges, a space between the leading surface of a first blade and a trailing surface of an adjacent blade defining a blood flow passage, the blades configured such that the blood flow passage area between successive blades is constant for all radii on the impeller; and a magnetic drive external to the housing, said magnetic drive system cooperating with the magnets disposed on the blades of the impeller to bias the impeller to rotate about its axis of rotation.

6. The blood pump of claim 5 wherein the impeller comprises three blades.

7. The blood pump of claim 5 wherein the support body is coextensive with the outer radius of the impeller.

8. The blood pump of claim 5 wherein the housing is substantially cylindrical.

9. The blood pump of claim 5 wherein the housing is substantially conical.

10. The blood pump of claim 5 wherein the leading edge at the inner radius precedes the leading edge at the outer radius in the direction of rotation of the impeller.

11. The blood pump of claim 5 wherein the leading edge at the outer radius precedes the leading edge at the inner radius in the direction of rotation of the impeller.

12. The blood pump of claim 5 wherein the magnetic drive comprises a drive rotor rotating about the impeller axis of rotation, the drive rotor comprising magnets aligned with said magnets on the blades of the impeller for driving the impeller within the housing.

* * * * *